(12) United States Patent
Boyden et al.

(10) Patent No.: US 10,563,257 B2
(45) Date of Patent: *Feb. 18, 2020

(54) IN SITU NUCLEIC ACID SEQUENCING OF EXPANDED BIOLOGICAL SAMPLES

(71) Applicants: Massachusetts Institute of Technology, Cambridge, MA (US); President and Fellows of Harvard College, Cambridge, MA (US)

(72) Inventors: Edward Stuart Boyden, Chestnut Hill, MA (US); Fei Chen, Cambridge, MA (US); Shahar Alon, Cambridge, MA (US); George Church, Brookline, MA (US); Paul Warren Tillberg, Cambridge, MA (US); Adam Henry Marblestone, Arlington, MA (US); Evan R. Daugharthy, Cambridge, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,150

(22) Filed: Aug. 23, 2018

(65) Prior Publication Data

US 2019/0055597 A1 Feb. 21, 2019

Related U.S. Application Data

(63) Continuation of application No. 15/098,968, filed on Apr. 14, 2016, now Pat. No. 10,059,990.

(60) Provisional application No. 62/147,204, filed on Apr. 14, 2015.

(51) Int. Cl.
*C12Q 1/6874* (2018.01)
*C12Q 1/6806* (2018.01)

(52) U.S. Cl.
CPC ......... *C12Q 1/6874* (2013.01); *C12Q 1/6806* (2013.01)

(58) Field of Classification Search
CPC ............................ C12Q 1/6874; C12Q 1/6806
USPC ........................................................ 506/26
See application file for complete search history.

(56) References Cited

U.S. PATENT DOCUMENTS

| 5,952,232 | A | 9/1999 | Rothman |
| 6,271,278 | B1 | 8/2001 | Park et al. |
| 2002/0176880 | A1 | 11/2002 | Cruise et al. |
| 2003/0120231 | A1 | 6/2003 | Wang |
| 2005/0034990 | A1 | 2/2005 | Crooks et al. |
| 2005/0196702 | A1 | 9/2005 | Bryant et al. |
| 2006/0003356 | A1 | 1/2006 | Shaw et al. |
| 2006/0110760 | A1 | 5/2006 | Kim et al. |
| 2006/0115146 | A1 | 6/2006 | Ogura et al. |
| 2007/0023942 | A1 | 2/2007 | Andino et al. |
| 2007/0134902 | A1 | 6/2007 | Bertino et al. |
| 2008/0286360 | A1 | 11/2008 | Shoichet et al. |
| 2009/0011420 | A1 | 1/2009 | Barron et al. |
| 2009/0096133 | A1 | 4/2009 | Doyle et al. |
| 2009/0191627 | A1 | 7/2009 | Fadeev et al. |
| 2009/0241681 | A1 | 10/2009 | Machauf et al. |
| 2010/0041128 | A1 | 2/2010 | Banes et al. |
| 2010/0055161 | A1 | 3/2010 | Ahn |
| 2010/0056445 | A1 | 3/2010 | Sharma et al. |
| 2010/0068725 | A1 | 3/2010 | Armbruster et al. |
| 2011/0070604 | A1 | 3/2011 | Gimzewski et al. |
| 2011/0091922 | A1 | 4/2011 | Krishnan et al. |
| 2011/0291357 | A1 | 12/2011 | Boyle |
| 2012/0184670 | A1 | 7/2012 | Kobayashi et al. |
| 2012/0220478 | A1 | 8/2012 | Shaffer |
| 2012/0251527 | A1 | 10/2012 | Reiser |
| 2013/0045503 | A1 | 2/2013 | Miyawaki et al. |
| 2013/0203605 | A1 | 8/2013 | Shendure et al. |
| 2014/0087139 | A1 | 3/2014 | Rowley et al. |
| 2016/0252528 | A1 | 9/2016 | Sangarlingham et al. |
| 2016/0304952 | A1 | 10/2016 | Boyden et al. |

FOREIGN PATENT DOCUMENTS

| JP | 2005291759 A | 10/2005 |
| WO | 2014025392 A1 | 2/2014 |
| WO | 2017027367 | 2/2017 |
| WO | 2017027368 | 2/2017 |

OTHER PUBLICATIONS

Kaur, et al., Biochemistry 45, pp. 7347-7355 (2006).
Cai, et al., Nat Meth 10, pp. 540-547 (2013).
Zimmerman, et al., Adapting the stretched sample method from tissue profiling to imaging, Proteomics, 8, (2008), p. 3809-3815. (Year: 2008).
Chang, et al., Iterative expansion microscopy, Nature Methods, 14(6), (2017), p. 593-599, and supplemental info (4 pages, 11 pages total) (Year: 2017).
Chen, F., et al., "Expansion Microscopy," Science, vol. 347, No. 6221, p. 543, Jan. 2015.
Chen, F., et al., "Nanoscale Imaging of RNA with Expansion Microscopy," HHS Public Access Author Manuscript, vol. 13(8): pp. 679-684 (Aug. 2016).
Chen, F., et al., "Supplementary Material for Expansion Microscopy," Science, vol. 347, No. 6221, pp. 543-548, Jan. 2015.

(Continued)

*Primary Examiner* — Karla A Dines
(74) *Attorney, Agent, or Firm* — Elmore Patent Law Group, P.C.; Joseph Zucchero; Carolyn Elmore

(57) ABSTRACT

The invention provides in situ nucleic acid sequencing to be conducted in biological specimens that have been physically expanded. The invention leverages the techniques for expansion microscopy (ExM) to provide new methods for in situ sequencing of nucleic acids as well as new methods for fluorescent in situ sequencing (FISSEQ) in a new process referred to herein as "expansion sequencing" (ExSEQ).

7 Claims, 3 Drawing Sheets
(3 of 3 Drawing Sheet(s) Filed in Color)

(56) References Cited

OTHER PUBLICATIONS

Reinhart-King, C., et al., "The Dynamics and Mechanics of Endothelial Cell Spreading," Biophysical Journal, vol. 89, pp. 676-689, Jul. 2005.

Van Vliet, et al., The Biomechanics Toolbox: Experimental Approaches for Living Cells and Biomolecules, Acta Materialia 51: pp. 5881-5905, Aug. 23, 2003, [online], retrieved from the Internet, Oct. 23, 2015.

Batish, M., et al., "Neuronal mRNAs Travel Singly into Dendrites," PNAS, vol. 109(12): pp. 4645-4650 (2012).

Beliveau, B., et al. "Versatile design and synthesis platform for visualizing genomes with Oligopaint FISH probes," PNAS, vol. 109(52): pfa. 21301-21306 (2012).

Bruchez, M., et al., "Semiconductor nanocrystals as fluorescent biological labels," Science, vol. 281, pp. 2013-2016 (1998).

Buckley, P., et al., "Cytoplasmic Intron Sequence-Retaining Transcripts Can Be Dendritically Targeted via ID Element Retrotransposons," Neuron, vol. 69, pp. 877-884 (2011).

Buxbaum, A., et al., Single-Actin mRNA Detection in Neurons Reveals a Mechanism for Regulating Its Translatability, Science, vol. 343, pp. 419-422 (2014).

Cabili, M., et al., "Localization and abundance analysis of human lncRNAs at single-cell and single-molecule resolution," Genome Biology, vol. 16(20) (2015).

Cajigas, I. et al. "The local transcriptome in the synaptic neuropil revealed by deep sequencing and high-resolution imaging," Neuron 74, pp. 453-466 (2012).

Chen, K., et al., "Spatially resolved, highly multiplexed RNA profiling in single cells," Science. vol. 348(6233), aaa6090-aaa6090 (2015).

Choi, H., et al., "Next-Generation in Situ Hybridization Chain Reaction: Higher Gain, Lower Cost, Greater Durability," ACS Nano 8(5): pp. 4284-4294 (2014).

Choi, H., et al., "Programmable in situ amplification for multiplexed imaging of mRNA expression," Nature Biotechnology, 28(11): pp. 1208-1212 (2010).

Chozinski, T., et al., "Expansion microscopy with conventional antibodies and fluorescent proteins," . Nature Methods, vol. 13(6): pp. 485-491 (2016).

Clemson, C., et al., "An architectural role for a nuclear noncoding RNA: NEAT1 RNA is essential for the structure of paraspeckles," Molecular Cell, 33, 717-26 (2009).

Engreitz, J., et al. "The Xist lncRNA exploits three-dimensional genome architecture to spread across the X chromosome," Science 341, 1237973 (2013).

Femino, A., et al., "Visualization of Single RNA Transcripts in Situ," Science, vol. 280; pp. 585-590 (1998).

Feng, G., et al., "Imaging neuronal subsets in transgenic mice expressing multiple spectral variants of GFP," Neuron 28, pp. 41-51 (2000). 28,.

Fouz, M., et al., "Bright Fluorescent Nanotags from Bottlebrush Polymers with DNA-Tipped Bristles," ACS Central Science, vol. 1, pp. 431-438 (2015).

Freifeld, et al., Expansion Microscopy of Zebrafish for Neuroscience and Developmental Biology Studies, PNAS, pp. E10799-E10808 (2017).

Huisken, J., et al., "Optical Sectioning Deep Inside Live Embryos by Selective Plane Illumination Microscopy," Science. vol. 305, 1007-1009 (2004).

Jung, H., et al., "Axonal mRNA localization and local protein synthesis in nervous system assembly, maintenance and repair," Nat. Rev. Neurosci., vol. 13(5): pp. 308-324 (2012).

Ke, R., et al., "In situ sequencing for RNA analysis in preserved tissue and cells," Nature Methods, vol. 10(9): pp. 857-860 (2013).

Lee, J., et al., "Highly Multiplexed Subcellular RNA Sequencing in Situ," Science, vol. 343, pp. 1360-1363 (2014).

Lein, E., et al. "Genome-wide atlas of gene expression in the adult mouse brain," Nature, vol. 445, 168-76 (2007).

Levsky, J., et al., "Fluorescence in situ hybridization: past, present and future," Journal of Cell Science, 116, 2833-2838 (2003).

Lieberman-Aiden, E., et al., "Comprehensive mapping of long-range interactions reveals folding principles of the human genome," Science 326, pp. 289-293 (2009).

Lubeck, E., et al., "Single-cell in situ RNA profiling by sequential hybridization," Nature Methods, vol. 11(4): pp. 360-361 (2014).

Lubeck, E., et al., "Single-cell systems biology by super-resolution imaging and combinatorial labeling," Nature Methods, vol. 9, 743-8 (2012).

Mito, M., et al., "Simultaneous multicolor detection of RNA and proteins using super-resolution microscopy," Methods (2015). doi:10.1016/j.ymeth.2015.11.007.

Panning, B., et al., "X chromosome Inactivation is Mediated by by Xist RNA stabilization," Cell. vol. 90, 907-16 (1997).

Plath, K., et al., "Xist RNA and the mechanism of X chromosome inactivation," Annu. Rev. Genet. 36, 233-78 (2002).

Raj, A., et al., "Detection of individual endogenous RNA transcripts in situ using multiple singly labeled probes," Methods in Enzymology, vol. 472, pp. 365-386, (Elsevier Inc., 2010).

Raj, A., et al., Imaging individual mRNA molecules using multiple singly labeled probes. Nat. Methods 5(10: pp. 877-879 (2008).

Schindelin J., et al., "Fiji: an open-source platform for biological-image analysis," Nature Methods, vol. 9, pp. 676-682 (2012).

Shah, S., et al., "Single-molecule RNA detection at depth via hybridization chain reaction and tissue hydrogel embedding and clearing," Development in Review, (2016).

Steward, O., et al., "Compartmentalized synthesis and degradation of proteins in neurons," Neuron, vol. 40, pp. 347-359 (2003).

Steward, O., et al., Synaptic activation causes the mRNA for the leg Arc to localize selectively near activated postsynaptic sites on dendrites. Neuron, vol. 21, pp. 741-751 (1998).

Thevenaz, P., et al., "A pyramid approach to subpixel registration based on intensity," IEEE Trans. Image Process. 7, 27-41 (1998).

Tillberg, P., et al., "Protein-Retention Expansion Microscopy of Cells and Tissues Labeled Using Standard Fluorescent Proteins and Antibodies," Nature Biotechnology vol. 34(9): pp. 987-995 (2016).

Wang, F., et al., "RNAscope: A novel in situ RNA analysis platform for formalin-fixed, paraffin-embedded tissues," Journal of Molecular Diagnostics, vol. 14(1): pp. 22-29 (2012).

Zhang, D., et al., "Dynamic DNA nanotechnology using strand-displacement reactions," Nature Chemistry, vol. 3, pp. 103-113 (2011).

Strack, R., "Imaging: Bigger is better for super-resolution," Nature Methods, vol. 12(3), pp. 169-169 (2015).

Cao, W., "DNA Ligases and Ligase-Based Technologies," Clinical and Applied Immunology Reviews 2, pp. 33-43 (2001).

Subach F. V, Patterson, G. H., Renz, M., Lippincott-Schwartz, J. & Verkhusha, V. V. Bright monomeric photoactivatable red fluorescent protein for two-color super-resolution sptPALM of live cells. J. Am. Chem. Soc. 132, 6481-91 (2010).

Nilsson, M., et al., "RNA-Templated DNA Ligation for Transcript Analysis," Nucleic Acids Research, 29(2): pp. 578-581 (2001).

Park, Y., et al., Detection of Hepatitis C Virus RNA Using Ligation-Dependent Polymerase Chain Reaction in Formalin-Fixed, Paraffin-Embedded Liver Tissues, American Journal of Pathology, 149(5): pp. 1485-1491 (1996).

Laemmli, U. K. Cleavage of structural proteins during the assembly of the head of bacteriophage T4. Nature 227, 680-685 (1970).

Hunt, et al., High temperature antigen retrieval and loss of nuclear morphology: a comparison of microwave\rand autoclave techniques. J. Clin. Pathol. 49, 767-770 (1996).

Jekel, P. A., Weijer, W. J. & Beintema, J. J. Use of endoproteinase Lys-C from Lysobacter enzymogenes in protein sequence analysis. Anal. Biochem. 134, 347-354 (1983).

Wu, C. C., MacCoss, M. J., Howell, K. E. & Yates, J. R. A method for the comprehensive proteomic analysis of membrane proteins. Nat. Biotechnol. 21,532-8 (2003).

Sniegowski, J. A., Phail, M. E. & Wachter, R. M. Maturation efficiency, trypsin sensitivity, and optical properties of Arg96, Glu222, and Gly67 variants of green fluorescent protein. Biochem. Biophys. Res. Commun. 332, 657-63 (2005).

(56) References Cited

OTHER PUBLICATIONS

Bokman, S. H. & Ward, W. W. Renaturation of Aequorea gree-fluorescent protein. Biochem. Biophys. Res. Commun. 101, 1372-80 (1981).
Seneviratne, U. et al. S-nitrosation of proteins relevant to Alzheimer's disease during early stages of neurodegeneration. Proc. Natl. Acad. Sci. U. S. A. 1521318113—(2016). doi:10.1073/pnas.1521318113.
Huang, B., Jones, S. A., Brandenburg, B. & Zhuang, X. Whole-cell 3D Storm reveals interactions between cellular structures with nanometer-scale resolution. Nat. Methods 5, 1047-1052 (2008).
Rego, E. H. et al. Nonlinear structured-illumination microscopy with a photoswitchable protein reveals cellular structures at 50-nm resolution. Proc. Natl. Acad. Sci. U. S. A. 109, E135-43 (2012).
Bates, M., Huang, B., Dempsey, G. T. & Zhuang, X. Multicolor super-resolution imaging with photo-switchable fluorescent probes. Science 317, 1749-1753 (2007).
Bossi, M. et al. Multicolor far-field fluorescence nanoscopy through isolated detection of distinct molecular species. Nano Lett. 8, 2463-8 (2008).
Livet, J. et al. Transgenic strategies for combinatorial expression of fluorescent proteins in the nervous system. Nature 450, 56-62 (2007).
Schnell, U., Dijk, F., Sjollema, K. A. & Giepmans, B. N. G. Immunolabeling artifacts and the need for live-cell imaging. Nat. Methods 9, 152-158 (2012).
Hackstadt, T. Steric hindrance of antibody binding to surface proteins of Coxiella burnetti by phase I lipopolysaccharide. Infect Immun 56, 802-807 (1988).
Jimenez, N. & Post, J. A. A Novel Approach for Intracellular 3D Immuno-Labeling for Electron Tomography. Traffic 13, 926-933 (2012).
Randall, K. J. & Pearse, G. A dual-label technique for the immunohistochemical demonstration of T-lymphocyte subsets in formalin-fixed, paraffin-embedded rat lymphoid tissue. Toxicol. Pathol. 36, 795-804 (2008).
Kakimoto, K., Takekoshi, S., Miyajima, K. & Osamura, R. Y. Hypothesis for the mechanism for heat-induced antigen retrieval occurring on fresh frozen sections without formalin-fixation in immunohistochemistry. J Mol Histol 39, 389-399 (2008).
Wachter, R. M. & James Remington, S. Sensitivity of the yellow variant of green fluorescent protein to halides and nitrate. Curr. Biol. 9, R628-R629 (1999).
Carpenter, A. E. et al. CellProfiler: image analysis software for identifying and quantifying cell phenotypes. Genome Biol. 7, R100 (2006).
Kroon, D.-J. B-spline Grid, Image and Point based Registration. Matlab Cent. at <http://www.mathworks.com/matlabcentral/fileexchange/20057-b-spline-grid--image-and-point-based-registration>.
Lowe, D. G. Distinctive Image Features from Scale-Invariant Keypoints. Int. J. Comput. Vis. 60, 91-110 (2004).
Vedaldi, A. & Fulkerson, B. Vlfeat. in Proc. Int. Conf. Multimed.—MM '10 1469 (ACM Press, 2010). doi:10.1145/1873951.1874249.
English, B. P. & Singer, R. H. A three-camera imaging microscope for high-speed single-molecule tracking and super-resolution imaging in living cells. in SPIE Nanosci. + Eng. (Mohseni, H., Agahi, M. H. & Razeghi, M.) 955008 (International Society for Optics and Photonics, 2015). doi:10.1117/12.2190246.
Edelstein, A., Amodaj, N., Hoover, K., Vale, R. & Stuurman, N. Computer control of microscopes using µManager. Curr. Protoc. Mol. Biol. Chapter 14, Unit14.20 (2010).
Dedecker, P., Duwé, S., Neely, R. K. & Zhang, J. Localizer: fast, accurate, open-source, and modular software package for super-resolution microscopy. J. Biomed. Opt. 17, 126008 (2012).
Mortensen, K. I., Churchman, L. S., Spudich, J. A. & Flyvbjerg, H. Optimized localization analysis for single molecule tracking and super-resolution microscopy. Nat. Methods 7, 377-81 (2010).
Al, H., Shaner, N. C., Cheng, Z., Tsien, R. Y. & Campbell, R. E. Exploration of new chromophore structures leads to the identification of improved blue fluorescent proteins. Biochemistry 46, 5904-10 (2007).
Subach, O. M., Cranfill, P. J., Davidson, M. W. & Verkhusha, V. V. An Enhanced Monomeric Blue Fluorescent Protein with the High Chemical Stability of the Chromophore. PLoS One 6, e28674 (2011).
Goedhardt, J. et al. Structure-guided evolution of cyan fluorescent proteins towards a quantum yield of 93%. Nat. Commun. 3, 751 (2012).
Markwardt, M. L. et al. An improved cerulean fluorescent protein with enhanced brightness and reduced reversible photoswitching. PLoS One 6, e17896 (2011).
Heim, R., Prasher, D. C. & Tsien, R. Y. Wavelength mutations and posttranslational autoxidation of green fluorescent protein. Proc. Natl. Acad. Sci. U. S. A. 91, 12501-4 (1994).
Heim, R. & Tsien, R. Y. Engineering green fluorescent protein for improved brightness, longer wavelengths and fluorescence resonance energy transfer. Curr. Biol. 6, 178-82 (1996).
Rose, R. C. & Bode, A. M. Ocular ascorbate transport and metabolism. Comp. Biochem. Physiol. A. Comp. Physiol. 100, 273-85 (1991).
Cubitt, A. B., Woollenweber, L. A. & Heim, R. Understanding structure-function relationships in the Aequorea victoria green fluorescent protein. Methods Cell Biol. 58, 19-30 (1999).
Cormack, B. P., Valdivia, R. H. & Falkow, S. FACS-optimized mutants of the green fluorescent protein (GFP). Gene 173, 33-8 (1996).
Lam, A. J. et al. Improving FRET dynamic range with bright green and red fluorescent proteins. Nat. Methods 9, 1005-12 (2012).
Ormo, M. et al. Crystal structure of the Aequorea victoria green fluorescent protein. Science 273, 1392-5 (1996).
Nagai, T. et al. A variant of yellow fluorescent protein with fast and efficient maturation for cell-biological applications. Nat. Biotechnol. 20, 87-90 (2002).
Griesbeck, O., Baird, G. S., Campbell, R. E., Zacharias, D. A. & Tsien, R. Y. Reducing the environmental sensitivity of yellow fluorescent protein. Mechanism and applications. J. Biol. Chem. 276, 29188-94 (2001).
Shaner, N. C. et al. Improving the photostability of bright monomeric orange and red fluorescent proteins. Nat. Methods 5, 545-51 (2008).
Shcherbakova, D. M., Hink, M. A., Joosen, L., Gadella, T. W. J. & Verkhusha, V. V. An orange fluorescent protein with a large Stokes shift for single-excitation multicolor FCCS and FRET imaging. J. Am. Chem. Soc. 134, 7913-23 (2012).
Shaner, N. C. et al. Improved monomeric red, orange and yellow fluorescent proteins derived from *discosoma* sp. red fluorescent protein. Nat. Biotechnol. 22, 1567-72 (2004).
Shcherbo, D. et al. Far-red fluorescent tags for protein imaging in living tissues. Biochem. J. 418, 567-74 (2009).
Chu, J. et al. Non-invasive intravital imaging of cellular differentiation with a bright red-excitable fluorescent protein. Nat. Methods 11, 572-8 (2014).
Filonov, G. S. et al. Bright and stable near-infrared fluorescent protein for in vivo imaging. Nat. Biotechnol. 29, 757-61 (2011).
Gurskaya, N. G. et al. Engineering of a monomeric green-to-red photoactivatable fluorescent protein induced by blue light. Nat. Biotechnol. 24, 461-5 (2006).
McKinney, S. A., Murphy, C. S., Hazelwood, K. L., Davidson, M. W. & Looger, L. L. A bright and photostable photoconvertible fluorescent protein. Nat. Methods 6, 131-3 (2009).
Habuchi, S., Tsutsui, H., Kochaniak, A. B., Miyawaki, A. & van Oijen, A. M. mKikGR, a monomeric photoswitchable fluorescent protein. PLoS One 3, e3944 (2008).
Lee, J. H. et al., "Highly Multiplexed Subcellular RNA Sequencing in Situ", Sciencexpress, online http://www.sciencemag.org/content/early/recent, 6 pages (Science, vol. 343, Feb. 27, 2014.
Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.

cDNA Amplicon Capture ExSEQ:

Reverse Transcription Capture ExSEQ:

RNA Capture EXSEQ:

Legend:

These Steps Take Place Inside Hydrogel

IN SITU NUCLEIC ACID SEQUENCING OF EXPANDED BIOLOGICAL SAMPLES

RELATED APPLICATIONS

This application is a continuation application of U.S. application Ser. No. 15/098,968, filed Apr. 14, 2016, which claims the benefit of U.S. Provisional Application No. 62/147,204, filed Apr. 14, 2015. The entire teachings of the above applications are incorporated herein by reference.

GOVERNMENT SUPPORT

This invention was made with Government support under Grant Nos. NS087724 and P50 HG005550 awarded by the National Institutes of Health. The Government has certain rights in the invention.

BACKGROUND OF THE INVENTION

Ideally one would be able to identify, and localize, biomolecules such as DNA and RNA throughout all the cells throughout a tissue, with nanoscale precision. Such mechanistic maps would reveal how epigenomic configurations and transcriptomic programs are configured to mediate cellular as well as organ-scale emergent functions, and pathologies. They would also provide systematic datasets that could enable generation of unbiased hypotheses that could be tested via causal perturbation, for a wide variety of basic and applied biological questions.

Current tools do not permit this. Optical methods maintain the spatial location of molecules, but the number of biomolecules that can be studied simultaneously is limited. On the other hand, transcriptomic approaches allow the multiplexed measurement of potentially all the RNA and DNA molecules, but spatial information is lost in the process. For example, in brain tissues all the current RNA sequencing methods involve grinding up or dissociating the neurons before sequencing, thereby destroying all spatial information about the cells in relation to the tissue. Moreover, the subcellular location of the sequences inside the individual cells is also lost, including all the information about the RNA contents of the axons, dendrites, and synapses, which is crucial for the understanding of neuronal communication.

International patent application serial number PCT/US15/16788, which is incorporated herein by reference and Chen et al., Science, 347, 543 (2015), teach that the resolution of conventional microscopy can be increased by physically expanding specimens, a process termed 'expansion microscopy' also referred to herein as "ExM". The advantages to ExM include tissue clearing, resolution improvement, and higher tolerance to sectioning error due to the specimen expansion in the z-axis. In the ExM method, cultured cells, fixed tissue, or in principle other types of samples of interest, including biological materials, are infused with a composition, or chemical cocktail, that results in it becoming embedded in the sample material, and then the composition can be expanded isotropically, preferably with nanoscale precision, in three dimensions.

ExM physically magnifies tissues while preserving nanoscale isotropy. It would be desirable to leverage ExM to devise new methods for in situ sequencing of nucleic acids throughout all the cells in a tissue.

SUMMARY OF THE INVENTION

The invention provides in situ nucleic acid sequencing to be conducted in biological specimens that have been physically expanded. The invention leverages the techniques for expansion microscopy (ExM) to provide new methods for in situ sequencing of nucleic acids as well as new methods for fluorescent in situ sequencing (FISSEQ) in a new process referred to herein as "expansion sequencing" and also referred to herein as "ExSEQ".

BRIEF DESCRIPTION OF THE DRAWINGS

The patent or application file contains at least one drawing executed in color. Copies of this patent or patent application publication with color drawings will be provided to the Office upon request and payment of the necessary fee.

DETAILED DESCRIPTION OF THE INVENTION

Figure 1:
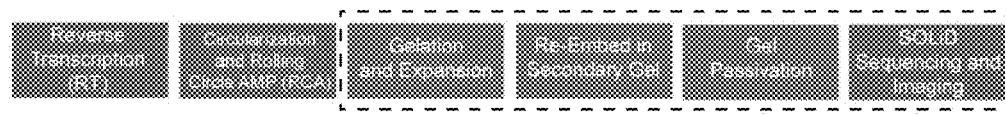
FIG. 1 is schematic illustrating workflows for several expansion sequencing methods in accordance with the invention.
Figure 1:
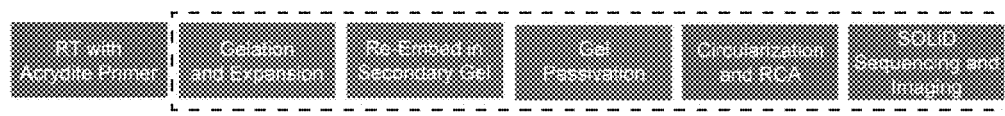
Figure 1:
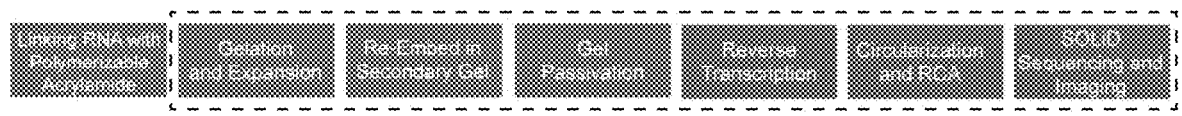
Figure 1:
Figure 1:

The terms "a", "an" and "the" as used herein are defined to mean "one or more" and include the plural unless the context is inappropriate.

The invention comprises a combination of in situ sequencing for example, FISSEQ and expansion microscopy (ExM) techniques in a new process referred to herein as expansion sequencing (ExSEQ). The existing FISSEQ technique, for example, is limited to detecting one target at a time per a diffraction limited spot. Expanding specimens before sequencing separates sequencing targets apart by a programmable volumetric factor, enabling detection of multiple species within a diffraction-limited-spot in a pre-expansion-space, using diffraction limited microscopy in a post-expansion space. This invention provides additional benefits, such as homogenizing the chemical environment (which is ~99% water throughout the specimen in the expanded state) and providing optical clarity.

In ExM, chemically fixed and permeabilized tissue is infused with swellable material, undergoes polymerization, and the tissue-polymer composite is treated with protease to homogenize its mechanical characteristics. Next, dialysis in water resulted in a isotropically ~4-fold linear expansion, thereby achieving super-resolution with diffraction-limited microscopes, enabling rapid image acquisition and large field of view (Chen et al., *Science*, 347, 543 (2015)). FISSEQ allows sequencing RNA molecules from intact, chemically fixed tissues, by enzymatically converting mRNAs in situ to amplicons of cDNA, which contain many copies of the original mRNA sequence. These sequences can be read out by sequentially ligating complementary fluorescently labeled nucleotides, with each nucleotide base read out via microscopy. Potentially, FISSEQ could provide a comprehensive snapshot of gene expression in a tissue, revealing the location and identity of every mRNA transcript in every cell. However, FISSEQ is currently challenging in tissues as the dense molecular environment significantly reduces the access of the required enzymes. Even in cell lines, only ~0.1% of mRNA transcripts are detected, mainly due to the need to carry out enzymatic reactions in situ (Lee et al., *Science*. 343, 1360-3 (2014)). Expansion allows individual RNA transcripts, normally densely packed, to be resolved spatially in a high-throughput manner, a fundamental requirement for FISSEQ. Furthermore, the expanded environment is 99% water, facilitating enzyme access and creating "quasi-in vitro" environment while retaining spatial information. Using expansion sequencing (ExSEQ), users can perform the enzymatic sequencing of RNA and DNA directly in expanded cells and tissues, with nanoprecise spatial resolution, enabling systematic cell type and cell state classification in health and disease.

Preferably, the invention provides a method for in-situ sequencing of target nucleic acids present in a biological sample comprising the steps of:
  a) attaching target nucleic acids present in the biological sample with a small molecule linker or nucleic acid adapter;
  b) embedding the biological sample in a swellable material wherein the small molecule linker or nucleic acid adaptor is attached both to the target nucleic acids present in the sample and to the swellable material,
  c) digesting proteins present in the biological sample;
  d) swelling the swellable material to form a first enlarged biological sample that is enlarged as compared to the biological sample;
  e) re-embedding the first enlarged sample in a non-swellable material;
  f) modifying the target nucleic acids or the nucleic acid adaptor to form a target nucleic acids or a nucleic acid adaptor useful for sequencing; and
  g) sequencing the nucleic acids present in the first enlarged sample.

Preferably, "modifying the target nucleic acids or the nucleic acid adapter" refers to biochemical modification, for example, contacting the target nucleic acids or the nucleic acid adapter with reverse transcriptase. Preferably, the sequencing step of step (g) is fluorescence in situ sequencing (FISSEQ). Preferably the method further comprises repeating steps (a) through (e) on the first enlarged sample to form a second enlarged sample prior to sequencing, a process also known as iterative expansion microscopy (iExM) disclosed in U.S. application Ser. No. 15/098,799 filed on Apr. 14, 2016, and incorporated herein by reference.

Preferably, the nucleic acid adaptors are attached to target nucleic acids via ligation to the target nucleic acid. Preferably, the nucleic acid adaptors are attached to target nucleic acids via a chemical reagent capable of reacting with amine groups on the target nucleic acid. Preferably, the small molecule linkers are attached to target nucleic acids via a chemical reactive group capable of covalently binding the target nucleic acid. Preferably, the method further comprises the step of passivating the first swellable material.

The term "nucleic acid" refers to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. "Nucleic acid" does not refer to any particular length of polymer. The term "sequence," in reference to a nucleic acid, refers to a contiguous series of nucleotides that are joined by covalent bonds (e.g., phosphodiester bonds).

The term "target nucleic acid" refers to a nucleic acid whose presence in a sample may be identified and sequenced. A target nucleic acid can be any nucleic to be selected and, optionally, amplified or sequenced preferably in combination with the nucleic acid adaptor. Target nucleic acids for use in the provided methods may be obtained from any biological sample using known, routine methods.

As used herein, the term "biological sample" means any biological sample that comprises, or is believed to comprise, nucleic acid sequences including, but not limited to, cDNA, mRNA and genomic DNA. Such samples may include tissues containing a variety of cells, a single cell or organelles. Suitable biological samples include, but are not limited to, a blood sample, biopsy specimen, tissue explant, organ culture, biological fluid or any other tissue or cell preparation, or fraction or derivative thereof or isolated therefrom. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multi-cellular organism or single-celled organism such as a eukaryotic (including plants and algae) or prokaryotic organism, archaeon, microorganisms (e.g., bacteria, archaea, fungi, protists, viruses), and aquatic plankton.

As used herein, the term "attach" or "attached" refers to both covalent interactions and noncovalent interactions. In certain embodiments of the invention, covalent attachment may be used, but generally all that is required is that the nucleic acids remain attached to the target nucleic acid under conditions for nucleic acid amplification and/or sequencing. Typically oligonucleotide adaptors are attached such that a 3' end is available for enzymatic extension and at least a portion of the sequence is capable of hybridizing to a complementary sequence. Attachment can occur via hybridization to the target nucleic acid, in which case the attached oligonucleotide may be in the 3'-5' orientation. Alternatively, attachment can occur by means other than base-pairing hybridization, such as the covalent attachment set forth above. The term "attach" may be used interchangeably herein with the terms, "anchor(ed)", affix(ed), link(ed) and immobilize(d).

As used herein, a "nucleic acid adaptor" is a nucleic acid sequence capable of attaching to a target nucleic acid and to the swellable material of the expansion gel. Preferably, attaching nucleic acid molecules to a target nucleic acid may be accomplished by ligation in situ. For example, anchorable DNA adaptors may be ligated to the 3' ends of the RNAs in the sample with RNA ligases, such as T4 RNA ligase, or may be attached via a chemical linker such as a reactive amine group capable of reacting with target nucleic acid. Additionally, acrylamide modified oligonucleotide primers may be covalently fixed within a swellable material such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule capable of attaching to a target nucleic acid and to the swellable material of the expansion gel. Preferably, attaching the small molecule to the target nucleic acid may be accomplished by chemical reactive group capable of covalently binding the target nucleic acid. For example, Label-IT® Amine (MirusBio) is a small molecule with alkylating group that primarily reacts to the N7 of guanine, thereby allowing covalent binding of RNA and DNA. Additionally, the small molecule (for example, Label-IT) can be acrylamide modified and therefore may be covalently fixed within a swellable material such as a polyacrylate gel. As used herein, the term "acrylamide modified" in reference to a small molecule linker means that the small molecule has an acrylamide moiety.

The term "biochemically modifying the target nucleic acids or the nucleic acid adaptor to form a target nucleic acids or a nucleic acid adaptor useful for sequencing" as used herein refers to converting the target nucleic acids or the nucleic acid adaptor to cDNA via reverse transcriptase, if necessary, and then circularizing the cDNA followed by subsequent amplification.

General sequencing methods known in the art, such as sequencing by extension with reversible terminators, fluorescent in situ sequencing (FISSEQ), pyrosequencing, massively parallel signature sequencing (MPSS) and the like are suitable for use in the methods of the invention. Reversible termination methods use step-wise sequencing-by-synthesis biochemistry that coupled with reversible termination and removable fluorescence.

FISSEQ is a method whereby DNA is extended by adding a single type of fluorescently-labelled nucleotide triphosphate to the reaction; washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described, for example in, (Lee et al., *Science*. 343, 1360-3 (2014).

Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) *Science* 281:363.

MPSS utilizes ligation-based DNA sequencing simultaneously. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al., (2000) *Nat. Biotech.* 18:630.

In a preferred embodiment, the biological sample can be labeled or tagged preferably with a detectable label. Typically, the label or tag will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis. Thus, the detectable label is preferably chemically attached to the biological sample, or a targeted component thereof. Preferably, the detectable label is an antibody and/or fluorescent dye wherein the antibody and/or fluorescent dye, further comprises a physical, biological, or chemical anchor or moiety that attaches or crosslinks the sample to the composition, hydrogel or other swellable material. Preferably the detectable label is attached to the nucleic acid adaptor. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

As used herein, the term "swellable material" generally refers to a material that expands when contacted with a liquid, such as water or other solvent. Preferably, the swellable material uniformly expands in 3 dimensions. Additionally or alternatively, the material is transparent such that, upon expansion, light can pass through the sample. Preferably, the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N, N-alkylene bisacrylamides). Precursors can also comprise polymerization initiators and crosslinkers.

In a preferred embodiment, the swellable polymer is polyacrylate or polyacrylamide and copolymers or crosslinked copolymers thereof. Alternatively or additionally, the swellable material can be formed in situ by chemically crosslinking water soluble oligomers or polymers. Thus, the invention envisions adding precursors (such as water soluble precursors) of the swellable material to the sample and rendering the precursors swellable in situ.

Preferably, "embedding" the sample in a swellable material comprises permeating (such as, perfusing, infusing, soaking, adding or other intermixing) the sample with the swellable material, preferably by adding precursors thereof. Alternatively or additionally, embedding the sample in a swellable material comprises permeating one or more monomers or other precursors throughout the sample and polymerizing and/or crosslinking the monomers or precursors to form the swellable material or polymer. In this manner the biological sample is embedded in the swellable material.

Preferably a biological sample, or a labeled sample, is permeated with a composition comprising water soluble precursors of a water swellable material and reacting the precursors to form the water swellable material in situ.

Preferably, the "re-embedding" comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the first enlarged sample, for example, is embedded in the non-swellable material. Embedding the expanded sample in a non-swellable material prevents conformational changes during sequencing despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

Preferably, the biological sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

As used herein the term "gel passivation" refers to the process for rendering a gel less reactive with the components contained within the gel such as by functionalizing the gel with chemical reagents to neutralize charges within the gel. For example, the carboxylic groups of sodium acrylate, which may be used in the swellable gel, can inhibit downstream enzymatic reactions. Treating the swellable gel composed of sodium acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel. After re-embedding in the non-swellable gel, the swellable gel may also be partially or completely degraded chemically, provided that the target nucleic acids can either stay anchored or can be transferred to the non-swellable gel.

Preferably, the biological sample and each enlarged sample thereafter is permeated with one or more monomers or a solution comprising one or more monomers or precursors which are then reacted to form a swellable or non-swellable polymerized gel depending on what step of the method is being performed. For example, if the biological sample is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

Once the sample, or labeled sample, is permeated, the solution is activated to form sodium polyacrylate. Preferably, the solution comprising the monomers is aqueous. The solution is preferably at high concentration, such as about 50% or more saturation (defined herein as the percentage of solids present in the aqueous solvent in the same ratio as would result in precipitation under the conditions of permeation). The solution is preferably at high concentration, such as about 75% or more saturation, more preferably 90% or more saturation.

Preferably, after the biological sample has been anchored to the swellable material, the sample is, optionally, subjected to a disruption of the endogenous biological molecules (or the physical structure of the biological sample, where the sample is other than a biological material), leaving the target nucleic acids with a small molecule linker or nucleic acid adapter, and the detectable labels such as fluorescent dye molecules, intact and anchored to the swellable material. In this way, the mechanical properties of the sample-swellable material complex are rendered more spatially uniform, allowing isotropic expansion with minimal artifacts.

As used herein, the "disruption of the endogenous physical structure of the sample" or the term "disruption of the endogenous biological molecules" of the biological sample generally refers to the mechanical, physical, chemical, biochemical or, preferably, enzymatic digestion, disruption or break up of the sample so that it will not resist expansion. Preferably, a protease enzyme is used to homogenize the sample-swellable material complex. It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample. Preferably the disruption of the physical structure of the sample is protein digestion of the proteins contained in the biological sample.

The sample-swellable material complex is then isoptripically expanded. Preferably, a solvent or liquid is added to the complex which is then absorbed by the swellable material and causes swelling. Where the swellable material is water swellable, an aqueous solution can be used.

In one embodiment, the addition of water allows for the embedded sample to expand at least 3 times, preferably 4 times, preferably 5 times, or more its original size in three-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. Surprisingly, as the material swells isotropically, the anchored tags maintain their relative spacial relationship.

The swollen material with the embedded biological sample can be imaged on any optical microscope, allowing effective imaging of features below the classical diffraction limit. Since the resultant specimen is preferably transparent, custom microscopes capable of large volume, Widefield of view, 3D scanning may also be used in conjunction with the expanded sample. The method also provides an optional step comprising amplification of the detectable label.

In accordance with the invention, chemically fixed and permeabilized biological specimens are embedded in a swellable gel material, subjected to a treatment to disrupt native biological networks, and then expanded. A sequence of enzymatic and/or chemical steps are carried out in order to anchor the target molecules into the swellable material and to prepare them for the sequencing reactions. Expansion can be carried out at one of several points in the sequence of preliminary reactions. The expanded gel is finally converted while expanded to a non-expanding state, by re-embedding in a non-expanding material. RNA or DNA molecules present in the sample may be sequenced using methods known to those familiar with the art, including sequencing by hybridization, ligation, and synthesis.

Nucleic Acid Anchoring:

For the FISSEQ process to be compatible with ExM, first nucleic acids, especially RNAs, cDNA, and/or DNA, have to be incorporated into the hydrogel network. We established two strategies for accomplishing this:

Ligation: DNA or RNA adapters with hydrogel anchorable groups (e.g. acrydite, 6-((Acryloyl)amino) hexanoic acid (Acryloyl-X) (Life Technologies)) can be ligated in situ. For example, anchorable DNA adaptors may be ligated to the 3' ends of the RNAs in the sample with RNA ligases, such as T4 RNA ligase. This can be done after RNA fragmentation (e.g., using RNase III), so that the resulting RNA fragments are short (~200-500 bases long) and contain 3'OH, which allows ligation with minimal side effects. In certain incarnations, these anchoring adapters may have additional roles in the preparation of the sequencing substrate, such as priming PCR or reverse transcription.

Anchoring in Via Chemical Reagents:

The commercial chemical reagent Label-IT® Amine (Minis Bio LLC), modified with hydrogel anchorable groups, (e.g., 6-((Acryloyl)amino)hexanoic acid (Acryloyl-X) (Life Technologies)), can be used for covalently securing RNA and DNA molecules directly to the ExM gel. The chemical and ligation approaches can also be used together. For example, the RNA or DNA can be anchored to the expanded gel with LABEL-IT® and then, in the expanded state, the RNA or DNA can be fragmented and ligated with RNA or DNA adapters.

In addition to the initial anchoring, the targets or any downstream products may be anchored at any point including in the native state or following any number of biochemical modifications such as reverse transcription or rolling circle amplification used to prepare targets for in situ sequencing (see FIG. 1).

Hydrogel Embedding:

Hydrogel embedding and expansion of tissue can be performed as described in ExM (International patent application serial number PCT/US15/16788 and Chen et al., Science, 347, 543 (2015)). Briefly: Monomer solution including sodium acrylate, acrylamide, and bisacrylamide, salt and buffer is mixed and prior to embedding, monomer solution is cooled to 4° C. to prevent premature gelation. Ammonium persulfate (APS) initiator and tetramethylethylenediamine (TEMED) accelerator are added to the monomer solution up to 0.2% (w/w) each. For thick specimens, the inhibitor 4-hydroxy-2,2,6,6-tetramethylpiperidin-1-oxyl (4-hydroxy-TEMPO) can be added to inhibit gelation during diffusion of the monomer solution into tissue sections. Cells or tissue slices can be incubated with the monomer solution plus APS/TEMED (and 4-hydroxy-TEMPO for thick sections) at 4° C. (for variable time depending on thickness) to allow monomer solution to diffuse, and then transferred to a humidified 37° C. incubator for 1-2 hours.

Alternative gel recipes, varying in monomer, crosslinker, initiator, accelerator, inhibitor and other additives can be used to tune the hydrogel properties such as expansion factor, chemical environment, and mechanical properties. These monomers include, acrylamide variants such as dimethylacrylamide, hydroxymethylacrylamide and acrylamide. Other free radical initiators such as VA-044 or UV activated (irgacure, riboflavin) may also be used.

Tissue Digestion, Expansion and Re-Embedding:

The cells are homogenized via proteolysis before the expansion. Proteinase K in digestion buffer (50 mM Tris (pH 8), 1 mM EDTA, 0.5% Triton X-100, 0.8 M guanidine HCl) can be applied directly to gels in at least ten times volume excess. The gels are then incubated in digestion buffer for at least 12 hours. During this step, formaldehyde crosslinks may also be reversed through heat, pH or chemical treatments.

Alternative methods of tissue disruption can be used, such as base or acid hydrolysis, and alternative proteinases. Digested gels can be next placed in excess volumes of doubly de-ionized water to expand. The expanded hydrogel, in the expanded state, is re-embedded within a non-expanding gel to prevent gel conformational changes during sequencing. For example, the non-expanding gel can be composed of acrylamide monomers, bisacrylamide, ammonium persulfate (APS) initiator and tetramethylethylenediamine (TEMED) accelerator.

Expanding Gel Passivation:

The carboxylic groups of sodium acrylate, used in the expanding gel, can inhibit downstream enzymatic reactions. Treating the sample with 1-Ethyl-3-(3-dimethylaminopropyl)carbodiimide (EDC) and N-Hydroxysuccinimide (NHS) allows primary amines, as ethanolamine, to covalently bind the carboxylic groups and passivate the expanding gel. The expanding gel may also be degraded chemically, after re-embedding in the non-expanding gel, provided that the anchored moieties are transferred to the re-embedding gel. Use of alternative non-charged hydrogel chemistries may also avoid charge passivation.

Incorporating FISSEQ Steps:

Following expansion, re-embedding and passivation, FISSEQ enzymatics steps can be carried out as previously described (Lee et al., Science. 343, 1360-3 (2014)). FISSEQ steps can be integrated for expansion at a variety of steps, see FIG. 1 for how the FISSEQ step order can be incorporated with expansion steps. Briefly, the anchored RNA is further biochemically modified into an in situ sequence-able substrate via reverse transcription, circularization of the cDNA, and subsequent amplification by phi29 polymerase, methods known to those familiar with the art. Sequencing by ligation or synthesis is used to identify the endogenous cDNA amplicons, and the molecules are also localized in 3D space. Localization may be converted into pre-expansion space using simple scaling transformations.

Other Applications of the Invention:

In addition to RNAs and DNAs, proteins, amino acid motifs, macromolecular complexes, and atomic configurations may be detected in situ using antigen-binding epitopes. These epitopes may be modified with a label for identification (such as a DNA barcode or fluorophore) as well as a methacryl group for co-polymerization with the expanding gel. Antigen-binding epitopes include antibodies, proteins, small molecules, and aptamers.

The present invention will be better understood in connection with the following Examples. However, it should be understood that these examples are for illustrative purposes only and are not meant to limit the scope of the invention. Various changes and modifications will be apparent to those skilled in the art and such changes and modifications including, without limitation, those relating to the formulations and/or methods of the invention may be made without departing from the spirit of the invention and the scope of the appended claims.

EXAMPLES

Example 1

Figure 2:
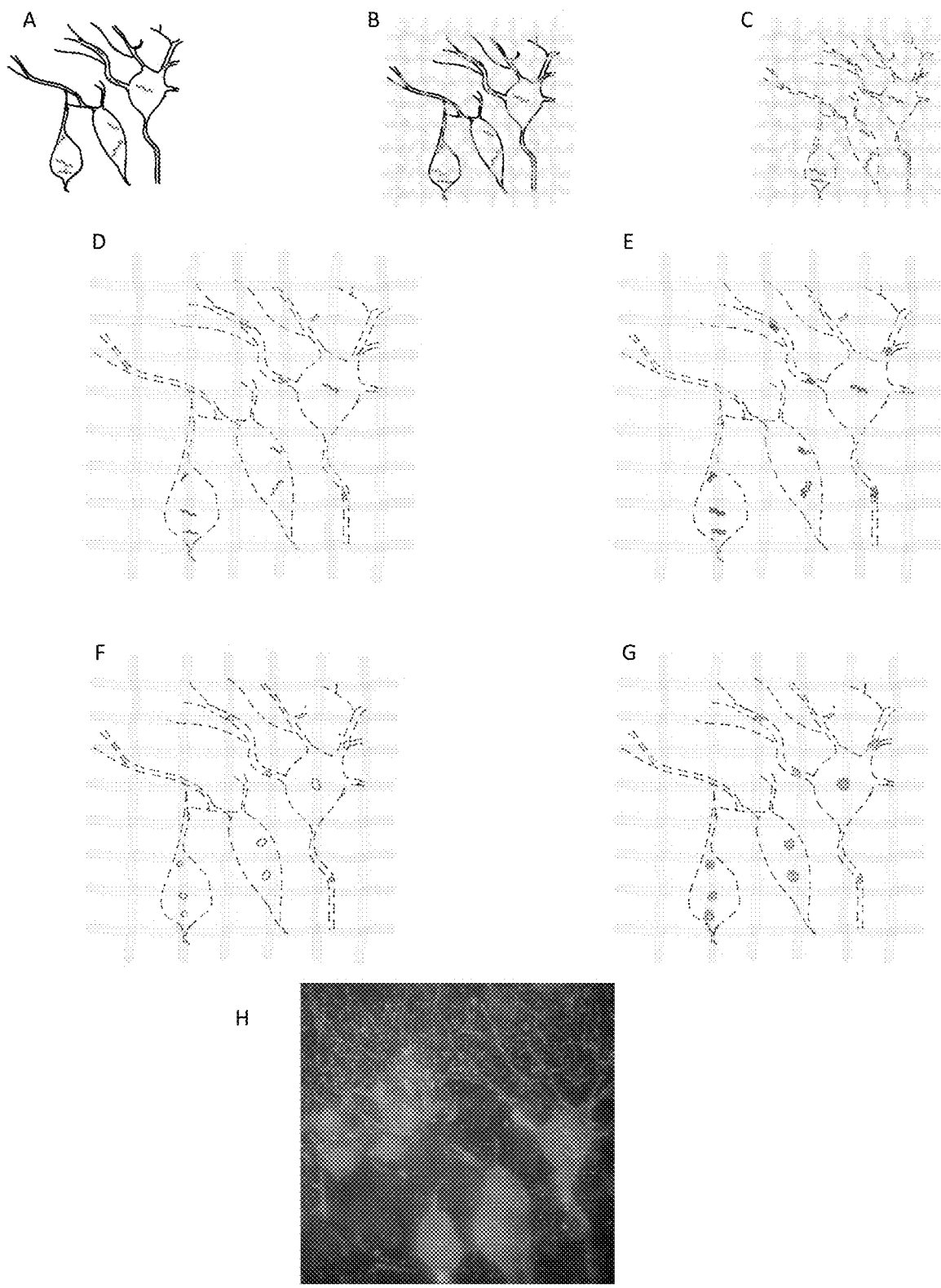
FIG. 2 is a schematic showing in situ expansion sequencing conducted on biological samples that have been physically expanded: Panel A depicts that the RNA molecules are tagged; Panel B depicts that biological specimens are embedded in a swellable gel material; Panel C depicts disruption of the native biological networks; Panel D depicts expansion of the sample and that the tagged RNA molecules are incorporated into the swellable material; Panel E depicts using the FISSEQ method, RNA molecules present in the sample are reverse transcribed to cDNA; Panel F depicts that RNA molecules are circularized using CircLigase; Panel G depicts RNA amplified using rolling circle amplification; Panel H depicts amplified cDNA (green) in expanded mouse hippocampus. Thy1-YFP mice were used, thereby allowing sparse neuronal labeling (red); the nuclei are DAPI-stained (blue); the amplified cDNA can now be sequenced in situ using sequencing by ligation.
Figure 3:
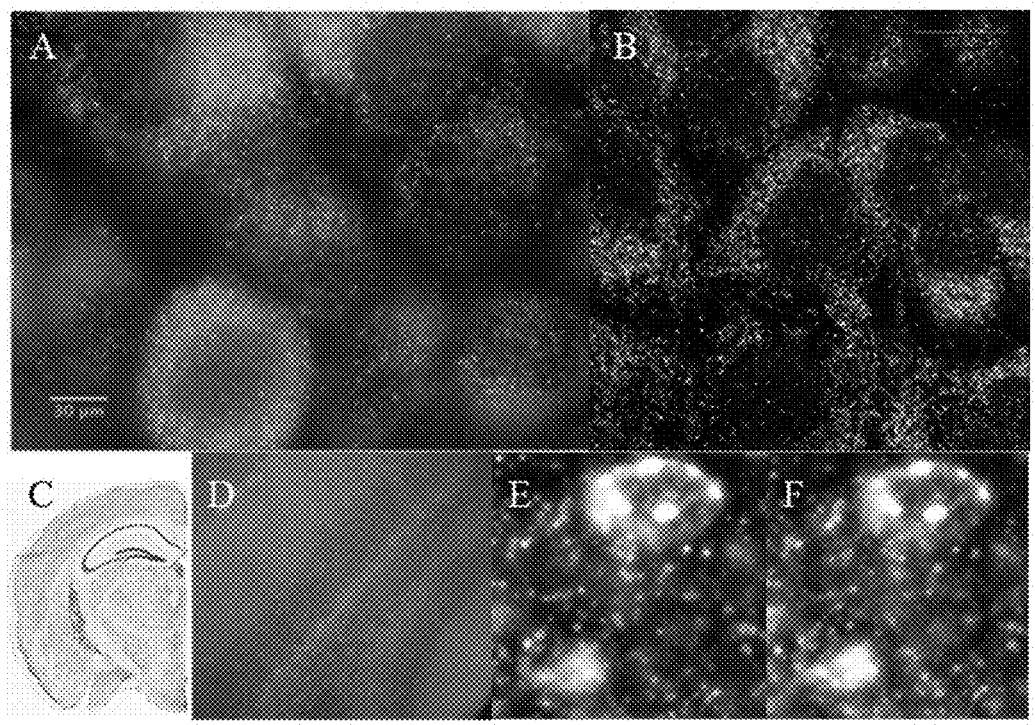
FIG. 3 shows microscopy images showing in situ sequencing in expanded human cell line and expanded mouse brain tissue. Panels A and D show amplified cDNA (green) in expanded human HeLa cell line (Panel A) and expanded mouse hippocampus (Panel D). The nuclei are DAPI-stained (blue). Panel C is a section of the mouse brain showing the hippocampus (from Allen Brain Atlas). Panels B, E and F show sequencing by ligation in expanded human HeLa cell line (Panel B) and expanded mouse hippocampus (Panels E and F). In each sequencing round different colors (blue, magenta, green, and red) reveal the current base of the amplified cDNA. Overall, 32 bases were sequenced from each amplified cDNA in the region of the expanded mouse hippocampus shown in (Panel D). Panel E shows sequencing of a region from the sample in Panel D. Panel F shows the next base of the sample from Panel E being sequenced.

Demonstration of ExSEQ:

To demonstrate ExSEQ, we have expanded human HeLa cell lines and a slice of mouse hippocampus and generated libraries of cDNA amplicons using the chemical RNA capture strategy (FIG. 2 and FIG. 3). Next, we sequenced 32 bases of the cDNA amplicons in expanded mouse hippocampus in situ (FIG. 3). As expected, most of the cDNA mapped to the correct annotated strand of known mRNA. Importantly, the highly expressed cDNA mapped to known neuronal genes, including neurotransmitter transporters, channels, and receptors. The yield obtained and the sequence identities of the cDNA provide evidence that ExSEQ can indeed quantify the transcriptome in expanded tissues in situ.

Brief materials and methods used to create the data described in FIGS. 2 and 3: for the mouse hippocampus data, Thy1-YFP (Tg(Thy1-YFP)16Jrs) male mice in the age range 6-8 weeks were anesthetized with isoflurane and perfused transcardially with ice cold 4% paraformaldehyde. Brains were dissected out, left in 4% paraformaldehyde at 4° C. for one day, before moving to PBS containing 100 mM glycine. 50 µm slices were sliced on a vibratome (Leica VT1000S) and stored at 4° C. in PBS until use. The slices were permeabilized in 0.25% Triton X-100 in PBS for 1 hour. For the HeLa (ATCC CCL-2) cell line data, the cells were cultured in Culturewell Chambered Coverglass (Invitrogen), fixed using 10% formalin in PBS for 15 min, and permeabilized in 0.25% Triton X-100 in PBS for 10 minutes.

To obtain the YFP labeling in FIG. 2, the brain samples were stained as in Chen et al., *Science,* 347, 543 (2015), that is, with primary antibody against GFP (Abeam, ab13970), followed by DNA-labeled secondary antibody, and finally with tri-functional label.

The small chemical LABEL-IT® Amine (Mirus Bio LLC), modified with hydrogel anchorable group (acryloyl-X), was used for RNA capturing. First, 1 mg/mL acryloyl-X was reacted with 1 mg/mL of LABEL-IT® Amine overnight at room temperature with shaking. Next, the samples were incubated with 0.02 mg/mL acryloyl-X-reacted LABEL-IT® in 20 mM MOPS buffer pH 7.7 at 37° C. overnight.

Hydrogel embedding, proteolysis, and expansion were performed as in Chen et al., *Science,* 347, 543 (2015).

To re-embed the samples in a non-swellable polymer, gels were incubated in 3% acrylamide, 0.15% N,N'-Methylenebisacrylamide with 0.075% APS, 0.075% TEMED and 5 mM Tris ph 10.5 for 20 minutes on a shaker. The gels were then placed in a humidified chamber that was purged with nitrogen gas. Finally the gels were moved to a 37° C. incubator for gelation for 1.5 hours.

The swellable gel was then passivated by treating the samples with 1-Ethyl-3-(3-dimethylaminopropyl)carbodiimide (EDC) and N-Hydroxysuccinimide (NETS) to covalently react ethanolamine to the carboxylic groups. First, the gels were incubated with 2M Ethanolamine hydrochloride, 150 mM EDC, 150 mM NETS, and 100 mM 2-(N-morpholino)ethanesulfonic acid (MES) buffer ph 6.5 for 2 hours. Next, the gels were incubated with 2M Ethanolamine hydrochloride and 62 mM Sodium borate (SB) buffer at pH 8.5 for 40 minutes.

Library preparation and nucleic acid sequencing, starting from reverse transcription, were performed as in Lee et al., *Science.* 343, 1360-3 (2014).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the preferred embodiments described herein are not mutually exclusive and that features from the various preferred embodiments may be combined in whole or in part in accordance with the invention.

What is claimed is:

1. A method for in-situ sequencing of target nucleic acids present in a biological sample comprising the steps of:
    a) linking target nucleic acids present in the biological sample with a small molecule linker or a nucleic acid adaptor capable of linking to a target nucleic acid and to a swellable material;
    b) embedding the biological sample comprising the target nucleic acids and attached small molecule linker or nucleic acid adaptor in a swellable material wherein the small molecule linker or the nucleic acid adaptor is linked to the target nucleic acids present in the sample and to the swellable material,
    c) digesting proteins present in the biological sample;
    d) swelling the swellable material to form a first enlarged biological sample that is enlarged as compared to the biological sample;
    e) re-embedding the first enlarged sample in a non-swellable material;
    f) modifying the target nucleic acids or the nucleic acid adaptor to form a nucleic acid adaptor useful for sequencing; and
    g) sequencing the nucleic acids present in the first enlarged sample.

2. The method of claim 1, wherein biochemically modifying the target nucleic acids or the nucleic acid adapter comprises contacting the target nucleic acids or the nucleic acid adapter with reverse transcriptase.

3. The method of claim 1, wherein the sequencing step of step (g) is fluorescence in situ sequencing.

4. The method of claim 1, further comprising repeating steps (a) through (e) on the first enlarged sample to form a second enlarged sample prior to sequencing.

5. The method of claim 1, wherein nucleic acid adaptors are linked to target nucleic acids via ligation to the target nucleic acid.

6. The method of claim 1, wherein the small molecule linkers are attached to target nucleic acids via a chemical reactive group capable of covalently binding the target nucleic acid.

7. The method of claim 1, further comprising the step of passivating the first swellable material after re-embedding the first enlarged sample in a non-swellable material.

* * * * *

UNITED STATES PATENT AND TRADEMARK OFFICE
CERTIFICATE OF CORRECTION

PATENT NO. : 10,563,257 B2
APPLICATION NO. : 16/110150
DATED : February 18, 2020
INVENTOR(S) : Boyden et al.

It is certified that error appears in the above-identified patent and that said Letters Patent is hereby corrected as shown below:

In the Specification

In Column 1, Lines 10-13, delete:
"This invention was made with Government support under Grant Nos. NS087724 and P50 HG005550 awarded by the National Institutes of Health. The Government has certain rights in the invention."

And insert:
-- This invention was made with government support under NS087724, HG008525, and HG005550 awarded by the National Institutes of Health. The government has certain rights in the invention. --

Signed and Sealed this
Twenty-fifth Day of November, 2025

John A. Squires
*Director of the United States Patent and Trademark Office*